US010433711B2

(12) United States Patent
Ogura et al.

(10) Patent No.: US 10,433,711 B2
(45) Date of Patent: Oct. 8, 2019

(54) CONNECTOR AND ENDOSCOPE SYSTEM

(71) Applicant: FUJIFILM Corporation, Tokyo (JP)

(72) Inventors: Ryosuke Ogura, Kanagawa (JP);
Kimitake Fukushima, Kanagawa (JP);
Kazuyoshi Hara, Kanagawa (JP);
Kunihiko Tanaka, Kanagawa (JP);
Koji Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 276 days.

(21) Appl. No.: 15/187,788

(22) Filed: Jun. 21, 2016

(65) Prior Publication Data
US 2017/0014019 A1 Jan. 19, 2017

(30) Foreign Application Priority Data
Jul. 14, 2015 (JP) .................................. 2015-140806

(51) Int. Cl.
*A61B 1/00* (2006.01)
*A61B 1/07* (2006.01)

(52) U.S. Cl.
CPC ...... *A61B 1/00126* (2013.01); *A61B 1/00016* (2013.01); *A61B 1/00029* (2013.01); *A61B 1/00114* (2013.01); *A61B 1/00117* (2013.01); *A61B 1/00119* (2013.01); *A61B 1/00124* (2013.01); *A61B 1/00128* (2013.01); *A61B 1/07* (2013.01); *A61B 1/00006* (2013.01)

(58) Field of Classification Search
CPC ............ A61B 1/00117; A61B 1/00119; A61B 1/00121; A61B 1/00124; A61B 1/00126; A61B 1/00128; A61B 1/00006

USPC .......................................................... 600/132
See application file for complete search history.

(56) References Cited

U.S. PATENT DOCUMENTS 5,701,155 A * 12/1997 Wood ....................... A61B 1/04
348/72
9,089,255 B2 7/2015 Kato
(Continued)

FOREIGN PATENT DOCUMENTS

JP H06165753 6/1994
JP H10-155740 6/1998
(Continued)

OTHER PUBLICATIONS

"Office Action of Japan Counterpart Application," dated Apr. 25, 2018, with English translation thereof,p. 1-p. 9.

*Primary Examiner* — Aaron B Fairchild
(74) *Attorney, Agent, or Firm* — JCIPRNET

(57) ABSTRACT

There are provided a connector of which manufacture and maintenance are easy and an endoscope system. A connector is a connector for an endoscope that is connected to a light source device. The connector includes a light guide part that guides illumination light, a wireless communication unit that wirelessly communicates with the light source device, a wireless power receiving unit that wirelessly receives power supplied from the light source device, and a housing that is formed in a flat shape in which a horizontal length is longer than a vertical length in a connection posture where the connector is connected to the light source device. The light guide part, the wireless communication unit, and the wireless power receiving unit are provided on a front surface of the housing, which faces the light source device, so as to be lined up in a horizontal direction.

20 Claims, 5 Drawing Sheets

(56) References Cited

U.S. PATENT DOCUMENTS

| | | | |
|---|---|---|---|
| 2005/0119527 A1* | 6/2005 | Banik | A61B 1/00059 600/117 |
| 2006/0116550 A1* | 6/2006 | Noguchi | A61B 1/015 600/132 |
| 2009/0058997 A1* | 3/2009 | Kato | H04N 7/183 348/65 |

FOREIGN PATENT DOCUMENTS

| | | |
|---|---|---|
| JP | 2005-312688 | 11/2005 |
| JP | 2006320381 | 11/2006 |
| JP | 2011-087800 | 5/2011 |
| JP | 2013-208187 | 10/2013 |

\* cited by examiner

CONNECTOR AND ENDOSCOPE SYSTEM

CROSS-REFERENCE TO RELATED APPLICATIONS

The present application claims priority under 35 U.S.C. § 119 to Japanese Patent Application No. 2015-140806, filed on Jul. 14, 2015. Each of the above application(s) is hereby expressly incorporated by reference, in its entirety, into the present application.

BACKGROUND OF THE INVENTION

1. Field of the Invention

The present invention relates to a connector for an endoscope that is connected to a light source device generating illumination light, and an endoscope system.

2. Description of the Related Art

A diagnosis, which uses an endoscope system comprising an endoscope, a light source device, and a processor device, is generally made in a medical field. The endoscope includes an insertion part that is inserted into a subject, and images an observation object (a mucous membrane or the like present in the subject) that is irradiated with illumination light generated by the light source device. The processor device generates the image of the observation object by using image signals that are obtained from the imaging of the observation object, and displays the image of the observation object in a monitor.

The endoscope is connected to the light source device and the processor device by a cable that is called a universal cable. The universal cable extends from an operation part (a grip section) of the endoscope, and a connector, which is to be connected to the light source device and the processor device, is provided at an end portion of the universal cable. Since the light source device and the processor device are formed separately, the connector generally branches to a connector (hereinafter, referred to as an optical connector) that is optically connected to the light source device and a connector (hereinafter, referred to as an electrical connector) that is electrically connected to the processor device. For example, the optical connector is provided with a light guide part (a light guide, an optical fiber, or the like) that guides illumination light generated by the light source device; and the electrical connector is provided with an electrical contact that sends and receives control signals, image signals obtained from imaging performed by the endoscope, and the like.

In recent years, the light source device and the processor device have been connected to each other and there has been a case in which the light source device and the processor device are substantially integrated with each other. In an endoscope system of which the light source device and the processor device are substantially integrated with each other, a connector is electrically connected to the processor device through, for example, the light source device. Accordingly, the connector is formed of a connector in which the optical connector and the electrical connector are integrated with each other.

For example, in a connector of an endoscope system disclosed in JP2011-087800A, an optical connector and an electrical connector are integrated with each other and a coil for wirelessly sending and receiving control signals and the like and a coil for wirelessly receiving power to be supplied are provided around a light guide part. For this reason, when the connector of the endoscope system disclosed in JP2011-087800A is connected to a light source device, illumination light emitted from the light source device can be guided by a light guide part and communication of control signals and the like and the supply of power to each part of the endoscope can be performed through the light source device. JP2013-208187A discloses an integrated connector that includes a communication unit (a short-distance wireless transmission unit in JP2013-208187A) provided on the vertically upper side of the light guide part.

The connector disclosed in JP2011-087800A is formed in a cylindrical shape as a whole, and the connector disclosed in JP2013-208187A is formed in the shape of a rectangular parallelepiped that is long in a vertical direction (hereinafter, referred to as a vertical type) in a posture in which the connector is connected to the light source device arranged horizontally (hereinafter, referred to as a connection posture). However, connectors having shapes different from the shapes of these connectors are also known. For example, a connector disclosed in JP-H10-155740A is not a connector in which an optical connector and an electrical connector are integrated with each other, but is formed in the shape of a rectangular parallelepiped that is long in a horizontal direction (hereinafter, referred to as a horizontal type) in a connection posture. Further, a connector disclosed in JP2005-312688A is connected to a light source device through an attachment that is called a conduit connection adapter, and is a substantially horizontal type as in JP-H10-155740A in a state in which the conduit connection adapter is connected.

SUMMARY OF THE INVENTION

Since the optical connector and the electrical connector are integrated with each other as in JP2011-087800A and JP2013-208187A, the structure of the connector in which the optical connector and the electrical connector are integrated with each other is complicated in comparison with a connector in the related art in which the optical connector and the electrical connector are formed separately.

Since separate connectors, that is, the optical connector and the electrical connector overlap with each other at one point, the manufacture and maintenance of the connector disclosed in JP2011-087800A are difficult. Furthermore, naturally, an optical member for allowing illumination light to be incident on the light guide part of the connector, a coil for communicating with the connector, a coil for supplying power to the connector, and the like should be disposed so as to be integrated at one point even in the light source device to which the connector is connected. For this reason, manufacture and maintenance are difficult also in this case.

Moreover, the light source device is generally formed in the shape of a rectangular parallelepiped of which a vertical length is shortest (a so-called horizontal type). For this reason, when the light guide part and the communication unit (the short-distance wireless transmission unit) are disposed so as to be lined up in the vertical direction as in the vertical type connector disclosed in JP2013-208187A, an optical member for allowing illumination light to be incident on the light guide of the connector and a communication unit (a short-distance wireless transmission unit) for communicating with the connector should be disposed at the smallest portion of the light source device in the vertical direction (a longitudinal direction) so as to be lined up. Accordingly, when a vertical type connector is employed as in JP2013-208187A, the manufacture and maintenance of the light source device are difficult. Further, the light guide part and the communication unit (the short-distance wireless transmission unit) can be disposed in the vertical type connector so as to be separated and lined up in the vertical direction, but the light guide part and the communication unit should be integrated with each other so as to correspond to the height of the light source device. For this reason, actually, the manufacture and maintenance of the vertical type connector are also not easy.

An object of the invention is to provide a connector in which an optical connector and an electrical connector are integrated with each other and an endoscope system that are more easily manufactured and subjected to maintenance than the connector and the endoscope system in the related art, such as in JP2011-087800A and JP2013-208187A.

A connector according to an aspect of the invention is a connector for an endoscope that is connected to a light source device generating illumination light. The connector comprises a light guide part that guides the illumination light, a wireless communication unit that wirelessly communicates with the light source device, a wireless power receiving unit that wirelessly receives power supplied from the light source device, and a housing that is formed in a flat shape in which a horizontal length is longer than a vertical length in a connection posture where the connector is connected to the light source device. The light guide part, the wireless communication unit, and the wireless power receiving unit are provided on a front surface of the housing, which faces the light source device, so as to be lined up in a horizontal direction.

It is preferable that the housing comprises clean connecting caps which are not directly connected to a conduit opened toward the observation object and unclean connecting caps which are directly connected to the conduit opened toward the observation object, and, in a case in which the clean connecting caps are provided on one side in the horizontal direction of the housing in the connection posture, the unclean connecting caps are provided on the other side thereof on which the clean connecting caps are not provided.

It is preferable that side surfaces and a rear surface of the housing are curved surfaces curved in at least a horizontal direction in the connection posture and the clean connecting caps and the unclean connecting caps are provided on the side surfaces or the rear surface of the housing.

It is preferable that the light guide part is provided at a position offset to one direction in the horizontal direction from a middle of the front surface of the housing in the connection posture.

It is preferable that the wireless power receiving unit is provided at a position offset to a direction opposite to the direction in which the light guide part is offset with respect to the middle of the front surface of the housing.

It is preferable that the wireless communication unit is provided in the middle of the front surface of the housing in the connection posture.

It is preferable that the connector further comprises a grip section that is gripped by a user in a case in which the user connects the connector to the light source device and the grip section protrudes from a rear surface of the housing in the connection posture.

It is preferable that the grip section is provided in the rear of the front surface of the housing in a connection direction in which the connector is connected to the light source device.

An endoscope system according to another aspect of the invention comprises: a light source device that generates illumination light; the connector including the light guide part guiding the illumination light, the wireless communication unit wirelessly communicating with the light source device, and the wireless power receiving unit wirelessly receiving power supplied from the light source device; and an endoscope that is connected to the light source device by the connector. A housing of the connector is formed in the flat shape in which the horizontal length is longer than the vertical length in the connection posture where the connector is connected to the light source device; and the light guide part, the wireless communication unit, and the wireless power receiving unit are provided on the front surface of the housing, which faces the light source device, so as to be lined up in the horizontal direction.

It is preferable that the housing includes clean connecting caps which are not directly connected to a conduit opened toward the observation object and unclean connecting caps which are directly connected to the conduit opened toward the observation object, the light source device includes a connection portion to which the connector is connected and which is provided on a front surface thereof, the connection portion is provided at a position offset to one direction in the horizontal direction from a middle of the front surface of the light source device, the unclean connecting caps are provided on a position of the housing offset to the direction same as the direction in which the connection portion is offset and the clean connecting caps are provided on a position of the housing offset to the direction opposite to the direction in which the connection portion is offset in the connection posture, and the unclean connecting caps are provided on a right side of the housing and the clean connecting caps are provided on a left side of the housing in the connection posture in a case in which the connection portion is provided on a right side of the middle of the front surface of the light source device.

It is preferable that the clean connecting caps are provided on a surface of the housing corresponding to a middle of a front surface of the light source device in the connection posture.

It is preferable that the clean connecting caps are provided on a surface of the housing corresponding to a middle of the front surface of the light source device in a case in which the number of the clean connecting caps is smaller than the number of the unclean connecting caps and the unclean connecting caps are provided on a surface of the housing corresponding to a middle of the front surface of the light source device in a case in which the number of the clean connecting caps is larger than the number of the unclean connecting caps.

According to a connector and an endoscope system of the invention, a housing of the connector is formed in a flat shape in which a horizontal length is longer than a vertical length in a connection posture where the connector is connected to a light source device, and a light guide part, a wireless communication unit, and a wireless power receiving unit are provided on a front surface of the housing, which faces the light source device, so as to be lined up in a horizontal direction. Accordingly, the endoscope system and the connector of the invention are an endoscope system and a connector in which an optical connector and an electrical connector are integrated with each other, but the manufacture and maintenance of the endoscope system and the connector of the invention are easier than in the related art.

DESCRIPTION OF THE PREFERRED EMBODIMENTS

Figure 1:
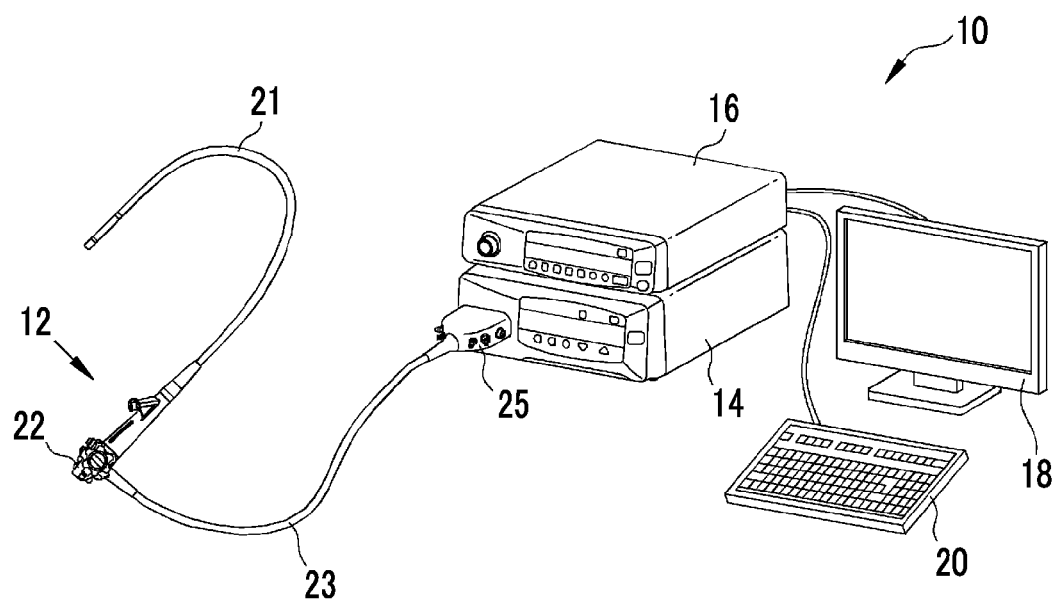
FIG. 1 is a view showing the appearance of an endoscope system.

As shown in FIG. 1, an endoscope system 10 includes an endoscope 12, a light source device 14, a processor device 16, a monitor 18, and a console 20. The endoscope 12 includes an insertion part 21 that is inserted into a subject, an operation part 22 that is provided at the base end portion of the insertion part 21, and a universal cable 23. The universal cable 23 is a cable in which a light guide part 31 (see FIG. 2) for guiding illumination light emitted from the light source device 14, a control line for controlling an imaging sensor provided at the tip of the insertion part 21, a signal line for sending image signals output from the imaging sensor during the imaging of an observation object irradiated with the illumination light, a power line for supplying power to each part such as the imaging sensor, and the like are integrated with each other. The universal cable 23 extends from the base end portion of the operation part 22, and a connector 25 connected to the light source device 14 is provided at the tip of the universal cable 23. The light guide part 31 of the endoscope 12 is a light guide that is a bundle of optical fibers.

The light source device 14 generates illumination light by a semiconductor light source, such as a LED (Light Emitting Diode) or a LD (Laser Diode), or a halogen lamp such as a xenon lamp. In a case in which the connector 25 is connected to the light source device 14, illumination light is incident on the light guide part 31 of the connector 25 and is applied to an observation object from the tip of the insertion part 21.

Further, the light source device 14 is electrically connected to the processor device 16, and the connector 25 of the endoscope 12 is also connected to the processor device 16 through the light source device 14 by being connected to the light source device 14. The sending and receiving of control signals, image signals, and the like between the light source device 14 and the connector 25 are wireless communication. For this reason, the light source device 14 transmits control signals and the like, which are wirelessly sent to and received from the connector 25, to the processor device 16. Furthermore, the light source device 14 supplies power, which is used to drive the imaging sensor and the like, to the connector 25, but the supply of this power is also performed wirelessly.

The processor device 16 controls the amount and light emitting timing of illumination light emitted from the light source device 14, the operation of the imaging sensor, and the like, and generates an endoscopic image by using image signals that are obtained from the imaging of the observation object irradiated with the illumination light. Further, the processor device 16 is electrically connected to the monitor 18 and the console 20. The monitor 18 displays the endoscopic image generated by the processor device 16, information about the endoscopic image, and the like. The console 20 is a user interface that receives an input operation, such as function setting.

Figure 2:
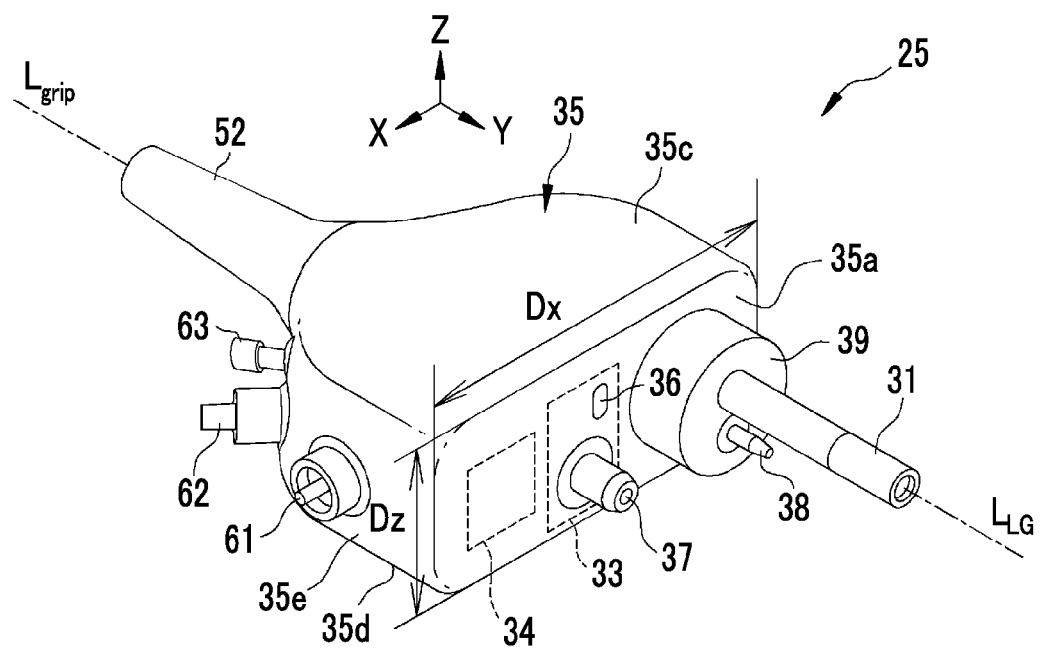
FIG. 2 is a perspective view showing the appearance of a connector.

As shown in FIG. 2, the connector 25 includes a light guide part 31 that guides illumination light, a wireless communication unit 33 that wirelessly communicates with the light source device 14, a wireless power receiving unit 34 that wirelessly receives power supplied from the light source device 14, and a housing 35 that houses the wireless communication unit 33 and the wireless power receiving unit 34; and is connected to the light source device 14. The housing 35 is formed in a flat shape in which a horizontal length Dx is longer than a vertical length Dz (Dx>Dz) in a connection posture where the connector 25 is connected to the light source device 14. That is, the connector 25 is a horizontal type.

A front surface 35a of the housing 35 is the tip surface of the connector 25, and is a surface facing the light source device 14 when the connector 25 is connected to the light source device 14. The light guide part 31, the wireless communication unit 33, and the wireless power receiving unit 34 are provided on the front surface 35a so as to be lined up in a horizontal direction. In the case of the connector 25, the light guide part 31 is provided on the left side on the front surface 35a, the wireless communication unit 33 is provided substantially in the middle of the front surface 35a, and the wireless power receiving unit 34 is provided on the right side on the front surface 35a. Note that, the left and the right in this embodiment mean a left direction and a right direction when the connector 25 arranged horizontally in the connection posture is viewed from a cover 52 side. Accordingly, in a case in which the connector 25 is connected to the light source device 14 that is arranged horizontally, the left and the right direction mean the horizontal direction.

In this specification, a posture where the connector 25 is correctly connected to the light source device 14 arranged horizontally is a "connection posture", a vertical direction with respect to the connection posture is referred to as a Z direction, a connection direction in which the connector 25 is connected to the light source device 14 in the connection posture is referred to as a Y direction, and a horizontal direction, which is perpendicular to the Z direction and the Y direction, is referred to as an X direction. The positive side in the Z direction is a vertically upper side; the positive side in the Y direction is a side where the light source device 14 is positioned when viewed from the connector 25; and the positive side in the X direction is a left side (the right side of the connector 25) when the front surface 35a of the connector 25 is viewed.

Figure 3:
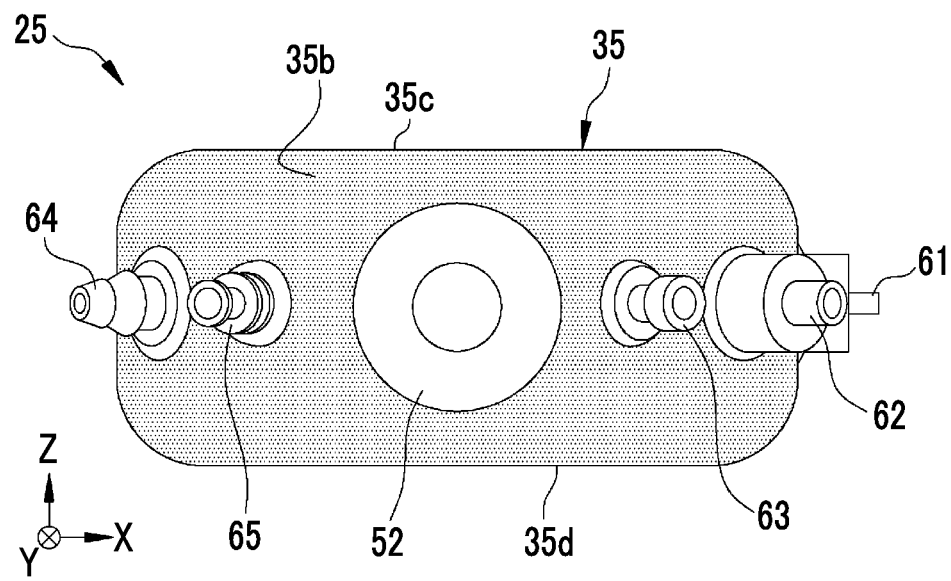
FIG. 3 is a view showing the rear surface of the connector.
Figure 4:
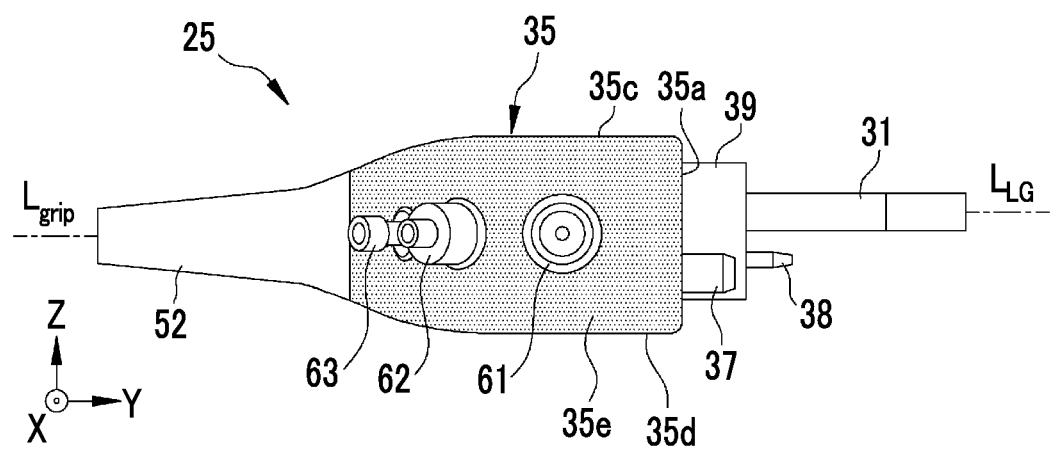
FIG. 4 is a view showing the right surface of the connector.
Figure 5:
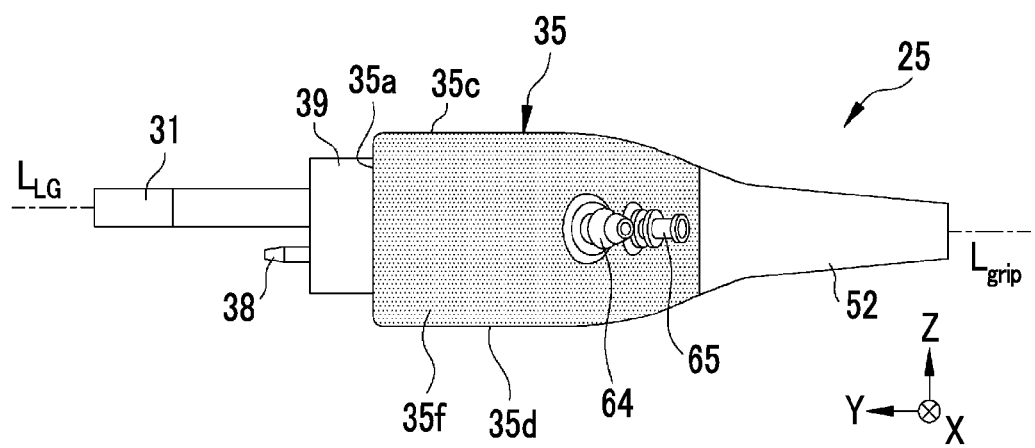
FIG. 5 is a view showing the left surface of the connector.

The surface of the housing 35 in the connection posture, which is viewed from the front side of the connector 25 (the positive side in the Y direction), is the front surface 35a, and the surface of the housing 35 in the connection posture, which is viewed from the rear side of the connector 25 (the negative side in the Y direction), is a rear surface 35b of the housing 35 as shown in FIG. 3 by hatching. Further, the surface of the housing 35 in the connection posture, which is viewed from the vertically upper side, is an upper surface 35c of the housing 35, and the surface of the housing 35 in the connection posture, which is viewed from the vertically lower side, is a lower surface 35d of the housing 35 (see FIG. 2). Furthermore, the surface of the housing 35 in the connection posture, which is viewed from the positive side in the X direction, is a right surface 35e of the housing 35 as shown in FIG. 4 by hatching, and the surface of the housing 35 in the connection posture, which is viewed from the negative side in the X direction, is a left surface 35f of the housing 35 as shown in FIG. 5 by hatching.

A rear portion (a portion corresponding to the negative side in the Y direction) of the housing 35 is formed in the shape of a substantially semi-circular disc. That is, an edge or the like, which clearly divides the right surface 35e and the rear surface 35b of the housing 35, is not formed, and the right surface 35e and the rear surface 35b are curved surfaces that are integrally and smoothly connected to each other. Likewise, the left surface 35f and the rear surface 35b of the housing 35 are curved surfaces that are integrally and smoothly connected to each other. Accordingly, among the curved surfaces that form the side surfaces and the rear surface of the housing 35, portions of the connector in the connection posture, which are viewed from the positive side and the negative side in the X direction, are referred to as the right surface 35e and the left surface 35f of the housing 35, and the surface of the connector in the connection posture, which is viewed from the negative side in the Y direction, is referred to as the rear surface 35b of the housing 35. For this reason, the right surface 35e and the rear surface 35b partially overlap each other, and the left surface 35f and the rear surface 35b partially overlap each other.

A pump connection portion 38 protrudes from a left portion (a portion corresponding to the negative side in the X direction) of the front surface 35a on the vertically lower side of the light guide part 31 in addition to the light guide part 31. A pump (not shown), which is provided in the light source device 14, is connected to the pump connection portion 38 when the connector 25 is connected to the light source device 14. Further, the pump connection portion 38 is connected to a conduit, such as an air/water supply channel, communicating with the connector 25, the universal cable 23, the operation part 22, and the insertion part 21. Furthermore, a fitting protrusion 39, which is fitted to a fitting recess 111 (see FIG. 7) provided on the light source device 14, is provided at the base end portion of the light guide part 31 and the pump connection portion 38, and the fitting protrusion 39 also protrudes from the front surface 35a. Since the light guide part 31 protrudes in the Y direction so as to be longer than the fitting protrusion 39, the light guide part 31 is visible when a user grips the connector 25. A central axis $L_{LG}$ of the light guide part 31 and the protruding direction of the pump connection portion 38 are parallel to the Y direction.

The wireless communication unit 33 includes: a control signal sending/receiving part 36 that wirelessly sends and receives control signals, which control the imaging sensor, and the like, to and from the light source device 14; and an image signal sending part 37 that wirelessly sends image signals, which are obtained from the imaging of the observation object irradiated with the illumination light, to the light source device 14. Wireless communication, which is performed by the control signal sending/receiving part 36 and the image signal sending part 37, is optical communication, and it is preferable that the wireless communication is, for example, near-infrared communication using near-infrared light (light having a wavelength in the range of about 0.7 μm to 2.5 μm). A connection terminal of the control signal sending/receiving part 36 is formed substantially on the front surface 35a, and a connection terminal of the image signal sending part 37 protrudes from the front surface 35a in parallel to the Y direction.

The wireless power receiving unit 34 is, for example, a coil (a so-called secondary coil), and receives power that is supplied from a coil (a so-called primary coil) of the light source device 14 by a non-contact power transmission method, such as an electromagnetic induction method or a magnetic field resonance method. In this case, since the wireless power receiving unit 34 is provided in the rear of the front surface 35a, the wireless power receiving unit 34 receives power supplied from the light source device 14 through the front surface 35a. The wireless power receiving unit 34 supplies power to each part of the endoscope 12, such as the imaging sensor.

The universal cable 23 is connected to the rear portion of the housing 35 (that is the rear surface 35b of the housing 35). The cover 52 covers a connection portion between the housing 35 and the universal cable 23. The rear portion of the housing 35 and the cover 52 function as a grip section that is gripped by a user in a case in which the user connects the connector 25 to the light source device 14 or a case in which the user removes the connector 25 from the light source device 14. The connection portion between the housing 35 and the universal cable 23 is positioned in the middle of the rear portion (the middle of the rear surface 35b) of the housing 35, and a central axis $L_{grip}$ of the cover 52 (hereinafter, referred to as a central axis $L_{grip}$ of the grip section) is parallel to the Y direction and passes through the center of the housing 35. Accordingly, a central axis $L_{LG}$ of the light guide part 31 is offset from the central axis $L_{grip}$ of the grip section to the negative side in X direction, and is offset to the positive side in the Y direction.

Further, the connector 25 has a function as a collective connection member (a so-called hub) that connects the endoscope 12 to the light source device 14 and the processor device 16 and also connects various peripheral members used during the use of the endoscope system 10 and the like. For this reason, the connector 25 is provided with a plurality of connecting caps that are connected to these various peripheral members.

Specifically, as shown in FIGS. 2, 3, and 4, a first connecting cap 61, a second connecting cap 62, and a third connecting cap 63 are provided on the right surface 35e (including the right portion of the rear surface 35b) of the housing 35. The first connecting cap 61 is a tank connector that is connected to a water supply tank (not shown). The first connecting cap 61 communicates with an air/water supply channel (not shown) through the water supply tank. The air/water supply channel is a conduit for sending air or water, which is stored in the water supply tank, toward an imaging window (in which a lens and an imaging sensor are disposed) that is provided at the tip of the insertion part 21. There is a possibility that the mucus and the like of the observation object enter an outlet (a so-called air/water supply port) of the air/water supply channel in a subject during the use of the endoscope system 10. However, since the first connecting cap 61 is connected to the air/water supply channel through the water supply tank, the mucus and the like of the observation object entering the air/water supply channel do not reach the first connecting cap 61. Accordingly, the first connecting cap 61 is a connecting cap that is clean without being contaminated by the mucus and the like of the observation object. Meanwhile, in this specification, "clean" means that the cap is not contaminated by the mucus and the like of the observation object in a case in which the endoscope system 10 is normally used, and "unclean" means that there is a possibility that the cap is contaminated by the mucus and the like of the observation object in a case in which the endoscope system 10 is normally used. In other words, it is considerable that caps which are not directly connected to a conduit opened toward the observation object are clean connecting caps and caps which are connected to the conduit opened toward the observation object are unclean connecting caps.

The second connecting cap 62 is a ventilation connector for a leakage test that checks the air leakage of the insertion part 21. Accordingly, the second connecting cap 62 communicates with the inside of the insertion part 21 and is not connected to a conduit that is opened toward the observation object. Further, the third connecting cap 63 is an S terminal to which an S cord is connected when a high-frequency treatment tool such as an electric scalpel is used. Accordingly, the third connecting cap 63 is not connected to a conduit that is opened toward the observation object. For this reason, the second connecting cap 62 and the third connecting cap 63 are connecting caps that are clean without being contaminated by the mucus and the like of the observation object. Accordingly, unclean connecting caps are not provided and only clean connecting caps are provided on the right surface 35e of the housing 35.

Meanwhile, as shown in FIGS. 3 and 5, a fourth connecting cap 64 and a fifth connecting cap 65 are provided on the left surface 35f (including the left portion of the rear surface 35b) of the housing 35. Specifically, the fourth connecting cap 64 is a suction cap and is connected to a suction tank. When the mucus and the like of the observation object are sucked, the sucked mucus and the like of the observation object enter the suction tank through the fourth connecting cap 64. Accordingly, the fourth connecting cap 64 is an unclean connecting cap. Further, the fifth connecting cap 65 is a water supply cap, and is connected to a water supply port (not shown) that ejects water and the like toward the observation object positioned at the tip of the insertion part 21. Since the fifth connecting cap 65 is directly connected to the water supply port without the water supply tank or the like, there is a possibility that the mucus and the like of the observation object enter the fifth connecting cap 65 and the fifth connecting cap 65 is contaminated. For this reason, the fifth connecting cap 65 is an unclean connecting cap. Accordingly, clean connecting caps are not provided and only unclean connecting caps are provided on the left surface 35f of the housing 35.

Figure 6:
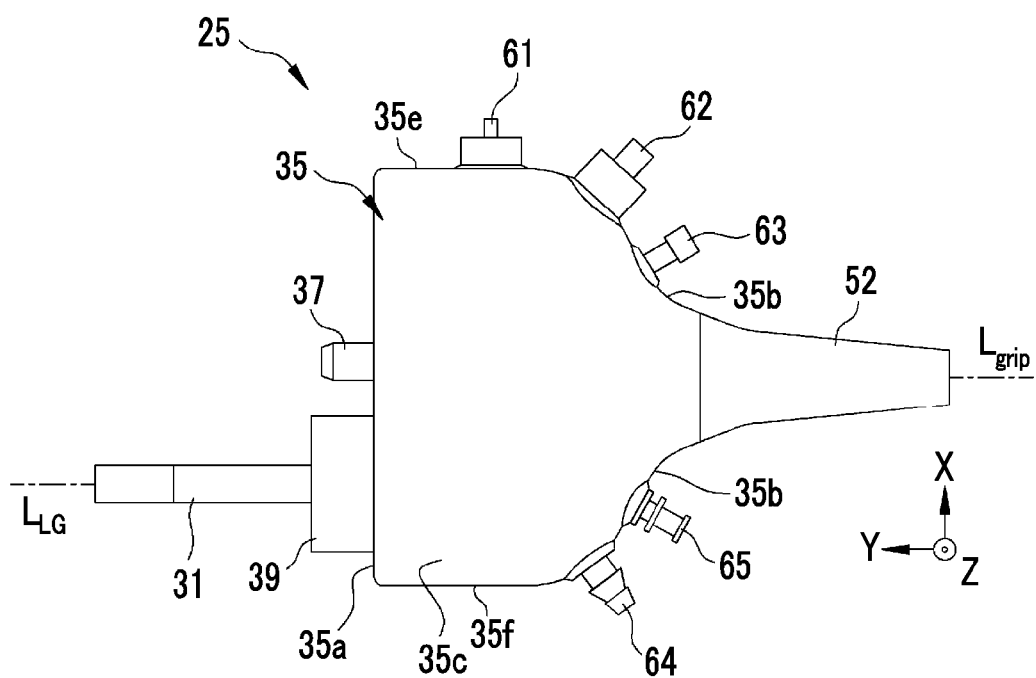
FIG. 6 is a top view of the connector.

As shown in FIG. 6, a portion of the housing 35, which extend over the rear surface 35b from the right surface 35e, is formed of a series of curved surfaces that are curved in the horizontal direction (a direction in an XY plane), and the first connecting cap 61, the second connecting cap 62, and the third connecting cap 63 protrude so as to be substantially perpendicular to the right surface 35e or the rear surface 35b. Likewise, a portion of the housing 35, which extend over the rear surface 35b from the left surface 35f, is formed of a series of curved surfaces that are curved in the horizontal direction, and the fourth connecting cap 64 and the fifth connecting cap 65 protrude vertically so as to be substantially perpendicular to the left surface 35f or the rear surface 35b. For this reason, the first connecting cap 61, the second connecting cap 62, the third connecting cap 63, the fourth connecting cap 64, and the fifth connecting cap 65 radially protrude from the housing 35.

Figure 7:
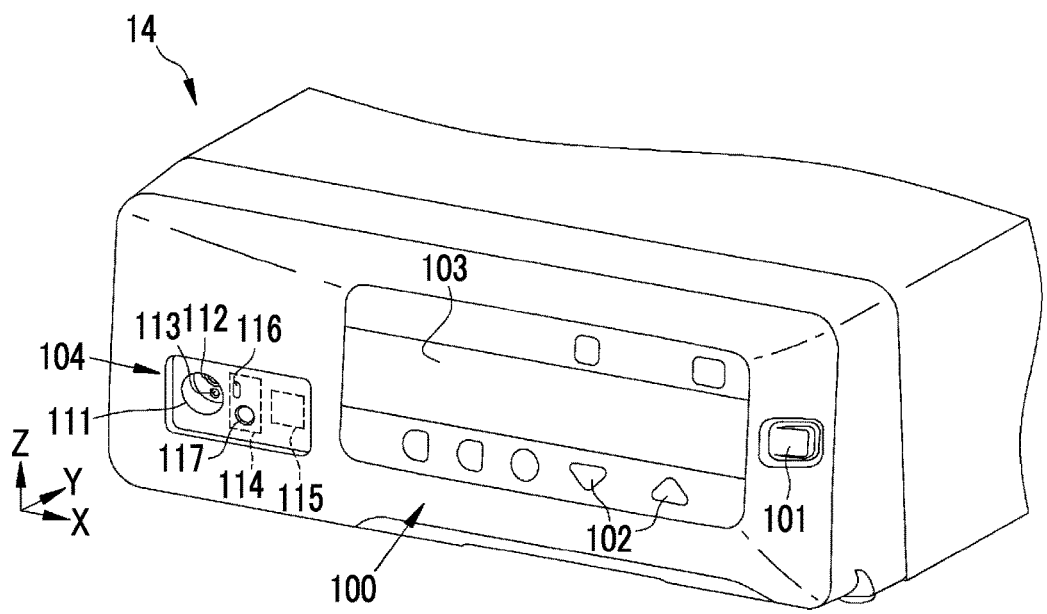
FIG. 7 is a perspective view showing the front surface of a light source device.

As shown in FIG. 7, the light source device 14 has the shape of a horizontal type rectangular parallelepiped that is shortest in the vertical direction, and a power button 101, operation buttons 102, and a display panel 103 are provided on a front surface 100 of the light source device 14 and a connection section 104 to which the connector 25 is connected is provided on the left side (the negative side in the X direction) on the front surface 100 (the positive side in the X direction). The connection section 104 comprises a light guide part-insertion opening 112 into which the light guide part 31 of the connector 25 is inserted, a wireless communication unit 114 that wirelessly communicates with the wireless communication unit 33 of the connector 25, and a wireless power supply unit 115 that wirelessly supplies power to the wireless power receiving unit 34 of the connector 25. The light guide part-insertion opening 112, the wireless communication unit 114, and the wireless power supply unit 115 are provided so as to be lined up in the horizontal direction (the X direction).

A fitting recess 111 to which the fitting protrusion 39 of the connector 25 is fitted is provided at the leftmost end of the connection section 104 (an end corresponding to the negative side in the X direction), and the light guide part-insertion opening 112 is provided in the fitting recess 111. Further, a pump connection portion-insertion opening 113 into which the pump connection portion 38 of the connector 25 is inserted is provided in the fitting recess 111 on the vertically lower side of the light guide part-insertion opening 112.

The wireless communication unit 114 of the light source device 14 is provided between the light guide part-insertion opening 112 and the wireless power supply unit 115 in the connection section 104. That is, the wireless communication unit 114 of the light source device 14 is provided in the middle of the connection section 104. The wireless communication unit 114 comprises: a control signal sending/receiving part 116 that wirelessly sends and receives control signals, which control the imaging sensor and the like, to and from the control signal sending/receiving part 36 of the connector 25; and an image signal receiving part 117 that receives image signals from the image signal sending part 37 of the connector 25. Since the image signal sending part 37 of the connector 25 protrudes from the front surface 35a, the image signal receiving part 117 is formed in the shape of a hole into which the protruding image signal sending part 37 is inserted.

The wireless power supply unit 115 is provided at the rightmost end (the positive side in the X direction) of the connection section 104. The wireless power supply unit 115 is, for example, a coil (a so-called primary coil), and supplies power to the wireless power receiving unit 34 of the connector 25 by a non-contact power transmission method, such as an electromagnetic induction method or a magnetic field resonance method.

Since the endoscope 12 is connected to the light source device 14 and the processor device 16 by the connector 25 and the connection section 104 formed as described above, the manufacture and maintenance of the endoscope system 10 are easier than the related art. Specifically, first, since the connector 25 is a horizontal type and the shape of the housing 35 is a flat shape in which a horizontal length Dx is longer than a vertical length Dz, the light guide part 31, the wireless communication unit 33, and the wireless power receiving unit 34 can be disposed on the front surface 35a of the housing 35 so as to be lined up in the horizontal direction. That is, the connector 25 has a margin for a space in which the light guide part 31, the wireless communication unit 33, and the wireless power receiving unit 34 are disposed, in comparison with a case in which the light guide part 31, the wireless communication unit 33, and the wireless power receiving unit 34 are provided at one point so as to overlap with each other. Accordingly, even though an optical connector and an electrical connector are integrated with each other, the internal structure of the connector is not extremely complicated and the manufacture and maintenance of the connector are easy.

Likewise, since the connector 25 is a horizontal type and the light guide part 31, the wireless communication unit 33, and the wireless power receiving unit 34 are disposed on the front surface 35a of the housing 35 so as to be lined up in the horizontal direction, the light guide part-insertion opening 112, the wireless communication unit 114, and the wireless power supply unit 115 can also be disposed in the connection section 104 of the light source device 14 by a wide margin so as to be lined up in the horizontal direction. The light source device 14 is also a horizontal type and the space in the light source device 14 is most limited in the vertical direction. Accordingly, when the light guide part-insertion opening 112, the wireless communication unit 114, and the wireless power supply unit 115 are disposed so as to be lined up in the horizontal direction as described above, the internal structure of the light source device 14 is not extremely complicated and the manufacture and maintenance of the light source device are easy even though not only the light guide part-insertion opening 112 but also the wireless communication unit 114 and the wireless power supply unit 115 are provided in the light source device 14.

In addition, since the connector 25 is a horizontal type and the light guide part 31, the wireless communication unit 33, and the wireless power receiving unit 34 are disposed on the front surface 35a of the housing 35 so as to be lined up in the horizontal direction, the length (the length in the Y direction) of the connector 25 protruding from the light source device 214 can be reduced when the connector 25 is connected to the light source device 214. For example, when the connector is formed in a cylindrical shape and the light guide part 31, the wireless communication unit 33, and the wireless power receiving unit 34 are collectively provided at one point so as to overlap with each other, some of members forming the light guide part 31, the wireless communication unit 33, and the wireless power receiving unit 34, or wires, circuits and the like connected to the light guide part 31, the wireless communication unit 33, and the wireless power receiving unit 34 should be disposed in the rear portion of the connector (the negative side in the Y direction). Accordingly, when the connector is formed in a cylindrical shape, the connector becomes long in the Y direction. In contrast, in the case of the horizontal type connector 25, some of members forming the light guide part 31, the wireless communication unit 33, and the wireless power receiving unit 34, or wires, circuits and the like connected to the light guide part 31, the wireless communication unit 33, and the wireless power receiving unit 34 can also be reasonably disposed in the horizontal direction of the housing 35 (the X direction) on the front surface 35a of the housing 35. Accordingly, the length of the connector 25 in the Y direction can be made shorter than that of a cylindrical connector.

Further, the connector 25 includes the first connecting cap 61, the second connecting cap 62, and the third connecting cap 63, which are clean and provided on the right surface 35e of the housing 35 or the right portion of the rear surface 35b, and the fourth connecting cap 64 and the fifth connecting cap 65 that are unclean and disposed so as to be concentrated on the left surface 35f of the housing 35 or the left portion of the rear surface 35b. Accordingly, the endoscope system 10 is easier to use than the endoscope system in the related art. For example, a water supply tank or an S terminal is connected to the first connecting cap 61 or the third connecting cap 63 at the time of the start of the observation using the endoscope, but is not removed or replaced much until the completion of the observation using the endoscope after the start of the observation using the endoscope. Meanwhile, there is a case in which a water supply mechanism, which supplies water toward the suction tank or the observation object, may be replaced as necessary even during the observation using the endoscope. That is, there are many cases in which clean connecting caps are not operated basically during the observation using the endoscope, and there is a case in which the removal and connection of unclean connecting caps are repeated even during the observation using the endoscope. Accordingly, when clean connecting caps are concentrated on one side of the connector 25 and unclean connecting caps are concentrated on the other side thereof as in the connector 25, a range in which a user detects a connection terminal to be removed or connected among a plurality of connecting caps is limited to the left surface 35f of the connector 25 and the left portion of the rear surface 35b. For this reason, since it is easy to find and operate a connection terminal that needs to be removed or connected, operability is good.

The reason why the connector 25 includes the first connecting cap 61, the second connecting cap 62, and the third connecting cap 63, which are clean and provided on the right surface 35e of the housing 35 or the right portion of the rear surface 35b, and the fourth connecting cap 64 and the fifth connecting cap 65 that are unclean and provided on the left surface 35f of the housing 35 or the left portion of the rear surface 35b is that the connection section 104 of the light source device 14 is positioned on the left side of the middle of the front surface 100 of the light source device 14 (the negative side in the X direction). In a case in which the connection section 104 of the light source device 14 is positioned on the left side of the middle of the front surface 100 of the light source device 14, a user commonly stands substantially on the left side of the light source device 14 and operates the endoscope 12. For this reason, when unclean connecting caps, which are necessary for operation, are disposed so as to be concentrated on the user side of the connector 25, usability is improved.

Figure 8:
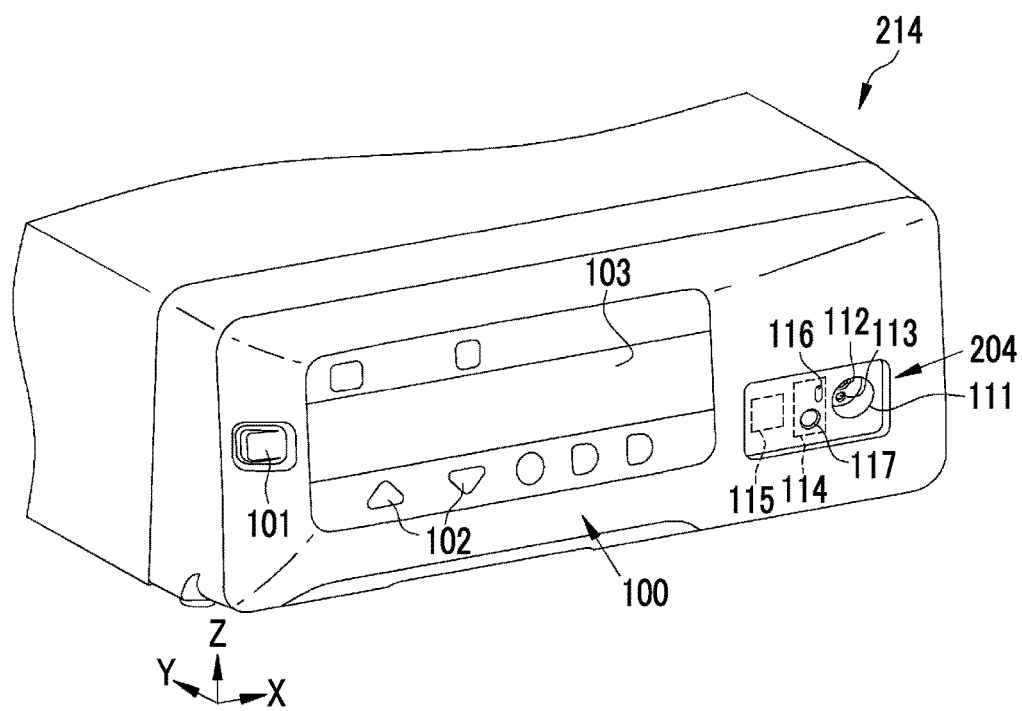
FIG. 8 is a perspective view showing the front surface of a light source device according to a modification.
Figure 9:
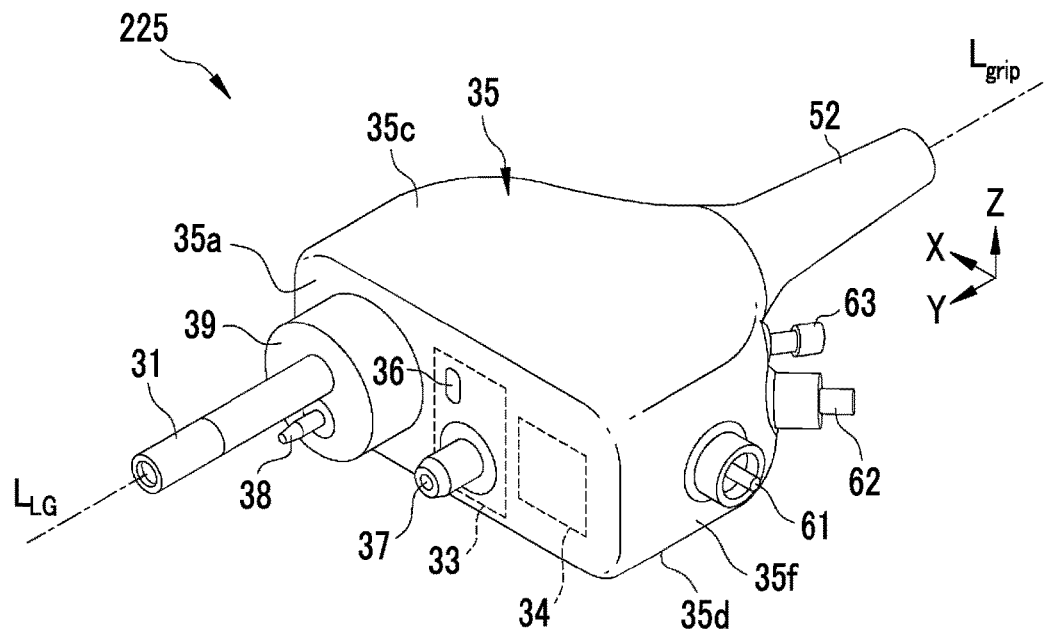
FIG. 9 is a perspective view showing the appearance of a connector according to the modification.
Figure 10:
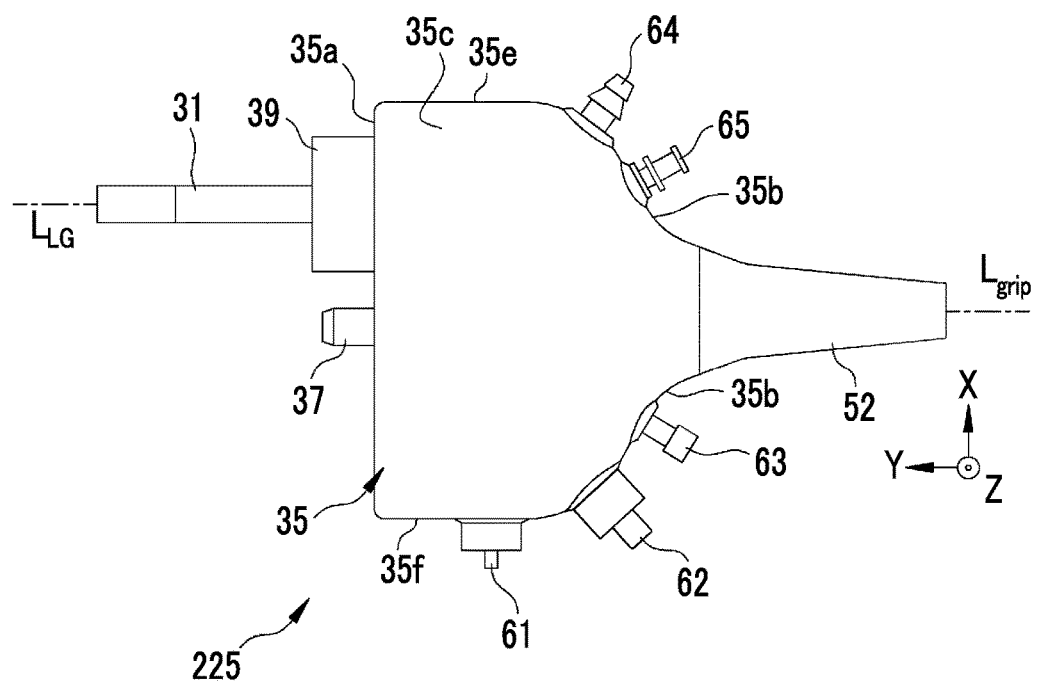
FIG. 10 is a top view of the connector according to the modification.

Accordingly, in a case in which the light source device 14 of the embodiment is horizontally inverted and a connection section 204 is positioned on the right side of the middle of a front surface 100 of a light source device 214 (the positive side in the X direction) as in the light source device 214 shown in FIG. 8, it is preferable that the connector 25 of the embodiment is also horizontally inverted (inverted with respect to a YZ plane), the fourth connecting cap 64 and the fifth connecting cap 65, which are unclean, are provided on the right surface 35e or the right portion of the rear surface 35b, and the first connecting cap 61, the second connecting cap 62, and the third connecting cap 63, which are clean, are provided on the left surface 35f or the left portion of the rear surface 35b as in a connector 225 shown in FIGS. 9 and 10. In the case of an endoscope system that includes the light source device 214 and the connector 225, a user commonly stands substantially on the right side of the light source device 214 (the positive side in the X direction) and operates the endoscope 12. For this reason, when unclean connecting caps, which are necessary for operation, are disposed so as to be concentrated on the user side of the connector 225, usability is improved as described above. That is, in a case in which the connection section 104 is provided at a position offset in one of the horizontal direction with respect to the middle of the front surface 100 of the light source device 214, it is preferable that unclean connecting caps are disposed so as to be concentrated in a same direction as the direction in which the connection section 104 is offset and clean connecting caps are disposed so as to be concentrated in a direction opposite to the direction in which the connection section 104 is offset.

That is, in a case in which there are unclean connecting caps and clean connecting caps, the unclean connecting caps may be provided so as to be concentrated on one of either the left side (the side corresponding to the left surface 35f) or the right side (the side corresponding to the right surface 35e) of the housing 35 in the connection posture and the clean connecting caps may be provided so as to be concentrated on the other thereof on which the unclean connecting caps are not provided. Further, it is referable that the clean connecting caps are disposed close to the middle of the front surface 100 of the light source device 14 and the unclean connecting caps are disposed close to the outside of the light source device 14 in the connection posture of the connector 25. More specifically, in a case in which the connection section 104 is positioned at the right end of the light source device 14 as in the light source device 14, the unclean connecting caps may be provided on the left side of the housing 35 and the clean connecting caps may be provided on the right side of the housing 35 as in the connector 25. Conversely, in a case in which the connection section 204 is positioned at the left end of the light source device 214 as in the light source device 214, the unclean connecting caps may be provided on the right side of the housing 35 and the clean connecting caps may be provided on the left side of the housing 35 as in the connector 225.

Furthermore, in the case of the connector 25, the clean connecting caps are three connecting caps, that is, the first connecting cap 61, the second connecting cap 62, and the third connecting cap 63, and the unclean connecting caps are two connecting caps, that is, the fourth connecting cap 64 and the fifth connecting cap 65. For this reason, the number of connecting caps, which protrude to the outside (the negative side in the X direction) more than the light source device 14, of the connector 25 is small. When the number of connecting caps, which protrude to the outside (the negative side in the X direction) more than the light source device 14, is made small as described above, the entire endoscope system 10 is compact even in a state in which the connector 25 is connected to the light source device 14. Accordingly, it is possible to reduce accidents in which persons or articles collide with the connecting caps of the connector 25 in a case in which a cart on which the light source device 14 and the processor device 16 are loaded is moved. As a result, it is possible to more safely and flexibly use the endoscope system 10. From this point of view, it is preferable that clean connecting caps are provided on the surface of the connector corresponding to the middle of the front surface 100 of the light source device 14 in a case in which the number of clean connecting caps is larger than the number of unclean connecting caps and unclean connecting caps are provided on the surface of the connector corresponding to the middle of the front surface 100 of the light source device 14 in a case in which the number of clean connecting caps is smaller than the number of unclean connecting caps. As a result, connecting caps of which the number is smaller are disposed so as to be concentrated on the side to which the connecting caps protrude to the outside more than the light source device 14. Accordingly, for example, in a case in which the connection section 204 is positioned on the left side of the middle of the front surface 100 of the light source device 214 as in the light source device 214 of FIG. 8 and a connector (not shown) of which the number of clean connecting caps is smaller than the number of unclean connecting caps is connected to the light source device 214, the unclean connecting caps may be disposed so as to be concentrated on the surface of the connector corresponding to the middle of the front surface 100 of the light source device 214 and the clean connecting caps may be disposed so as to be concentrated on the surface of the connector facing the outside of the light source device 214. In a case in which the number of clean connecting caps and the number of unclean connecting caps are equal to each other, it is preferable that the clean connecting caps are provided on the surface of the connector corresponding to the middle of the front surface 100 of the light source device 14 as described above and the unclean connecting caps are provided on the surface of the connector facing the outside of the light source device 14.

Meanwhile, since the first connecting cap 61, the second connecting cap 62, the third connecting cap 63, the fourth connecting cap 64, and the fifth connecting cap 65 are provided on the right surface 35e, the left surface 35f, and the rear surface 35b of the housing 35, that is, the curved surfaces curved in the horizontal direction and radially protrude from the housing 35, an interval between tips of the respective connecting caps is large in comparison with a case in which a plurality of connecting caps protrude from the housing 35 in parallel to each other. Accordingly, the connectivity of the connector 25 is better without the obstruction of adjacent connecting caps.

Further, the light guide part 31, the wireless communication unit 33, and the wireless power receiving unit 34, which are disposed on the front surface 35a of the housing 35 of the connector 25, are lined up in the horizontal direction in the order of the light guide part 31, the wireless communication unit 33, and the wireless power receiving unit 34 from the left side (the negative side in the X direction). However, the reason for this is that the connection section 104 of the light source device 14 is provided on the left side of the middle of the front surface 100 of the light source device 14. In a case in which the connector 25 is connected to the left portion of the light source device 14, a connection position where the connector 25 is connected to the light source device 14 is biased to the left side of the light source device 14 when being viewed from a user. For this reason, the user's awareness is likely to be concentrated on the left side. Further, when a breakdown caused by collision or the like occurs in the light guide part 31, the efficiency of the guide of illumination light deteriorates and observation using the endoscope is adversely affected. Accordingly, the light guide part 31 needs to be particularly carefully and accurately connected among the light guide part 31, the wireless communication unit 33, and the wireless power receiving unit 34 that are provided on the front surface 35a of the housing 35. For this reason, the light guide part 31 is provided at a position offset to the left side (the negative side in the X direction) from the middle of the housing 35 so that the light guide part 31 is easily and accurately inserted into the light guide part-insertion opening 112.

Likewise, according to the comparison between the wireless communication unit 33 and the wireless power receiving unit 34, the wireless communication unit 33 needs to be more carefully and accurately connected due to the fact that the image signal sending part 37 protrudes from the front surface 35a, the fact that a positional deviation or damage causes an error in sending and receiving signals since the control signal sending/receiving part 36 and the image signal sending part 37 send and receive signals through optical communication, and the like. For this reason, in the connector 25, the wireless communication unit 33 is provided in the vicinity of the middle of the front surface 35a on which awareness is likely to be concentrated second to the left side of the front surface 35a, and the wireless power receiving unit 34, which is not affected most by the accuracy of the connection position and the like, is provided at a position offset to the right side (the positive side in the X direction) from the middle of the housing 35.

Accordingly, in a case in which the connection section 204 is positioned at the right end of the light source device 214 as in the light source device 214 of FIG. 8, it is preferable that the light guide part 31 is provided at a position offset to the right side (the positive side in the X direction) of the middle of the front surface 35*a* of the housing 35, the wireless power receiving unit 34 is provided at a position offset to the left side (the negative side in the X direction) of the middle of the front surface 35*a*, and the wireless communication unit 33 is provided in the vicinity of the middle of the front surface 35*a* in the connector 225 connected to the connection section 204 as shown in FIGS. 9 and 10. That is, in regard to the connectors 25 and 225, it is preferable that the wireless power receiving unit 34 is provided at a position offset to the left side from the middle of the front surface 35*a* of the housing 35 in a case in which the light guide part 31 is provided at a position offset to the right side from the middle of the front surface 35*a* of the housing 35 in the connection posture and the wireless power receiving unit 34 is provided at a position offset to the right side from the middle of the front surface 35*a* of the housing 35 in a case in which the light guide part 31 is provided at a position offset to the left side from the middle of the front surface 35*a* of the housing 35 in the connection posture. Further, it is preferable that the wireless communication unit 33 is provided in the vicinity of the middle of the front surface 35*a* of the housing 35 (between the light guide part 31 and the wireless power receiving unit 34) in the connection posture.

It is preferable that the light guide part 31, the wireless communication unit 33, and the wireless power receiving unit 34 are disposed on the front surface 35*a* of the housing 35 so as to be lined up in the horizontal direction as described above, but it is preferable that the cover 52 functioning as the grip section protrudes from at least the rear surface 35*b* of the housing 35. The reason for this is that the connector 25 is easily held in comparison with a case in which the cover 52, which functions as the grip section protrudes from a position other than the rear surface 35*b*. Furthermore, the cover 52 may protrude toward the rear side (the negative side in the Y direction) from substantially the middle of the rear surface 35*b* in the Y direction that is the connection direction. The reason for this is that the connector 25 is easily held and the shift of a connection operation for moving the connector 25 toward the light source device 14 is small in comparison with a case in which the grip section is disposed at a position offset to the left or right side.

Meanwhile, in the embodiment, each of the connectors 25 and 225 is provided with the first connecting cap 61, the second connecting cap 62, and the third connecting cap 63, which are clean, and the fourth connecting cap 64 and the fifth connecting cap 65 that are unclean. However, the types and the number of the connecting caps, which are provided on the connector 25, are arbitrary. Clean connecting caps other than the first connecting cap 61, the second connecting cap 62, and the third connecting cap 63 may be provided, and unclean connecting caps other than the fourth connecting cap 64 and the fifth connecting cap 65 may be provided. The number of the clean connecting caps may be four or more or may be one or two. Further, clean connecting caps may not be provided in a case in which clean connecting caps are not needed. Likewise, the number of unclean connecting caps may be three or more or may be zero or one.

What is claimed is:

1. A connector for an endoscope that is configured to be connected to a light source device generating illumination light, the connector comprising:
   a light guide part that guides the illumination light;
   a wireless communication device that wirelessly communicates with the light source device, wherein the wireless communication device includes a control signal transceiver and an image signal emitter;
   a wireless power receiver that wirelessly receives power supplied from the light source device and comprises a coil that performs non-contract transmission; and
   a housing that is formed in a flat shape in which a horizontal length is longer than a vertical length in a connection posture where the connector is connected to the light source device,
   wherein the light guide part, the wireless communication device, and the wireless power receiver are provided on a front surface of the housing, which faces the light source device, so as to be lined up in a horizontal direction.

2. The connector for the endoscope that is configured to be connected to the light source device generating illumination light according to claim 1,
   wherein the housing comprises clean connecting caps which are not directly connected to a conduit opened toward an observation object and unclean connecting caps which are directly connected to the conduit opened toward the observation object, and
   in a case in which the clean connecting caps are provided on one side in the horizontal direction of the housing in the connection posture, the unclean connecting caps are provided on the other side thereof on which the clean connecting caps are not provided.

3. The connector for the endoscope that is configured to be connected to the light source device generating illumination light according to claim 2,
   wherein side surfaces and a rear surface of the housing are curved surfaces, which are curved in at least a horizontal direction, in the connection posture, and
   the clean connecting caps and the unclean connecting caps are provided on the side surfaces or the rear surface of the housing.

4. The connector for the endoscope that s configured to be connected to the light source device generating illumination light according to claim 3,
   wherein the wireless communication device is provided in the middle of the front surface of the housing in the connection posture.

5. The connector for the endoscope that is configured to be connected to the light source device generating illumination light according to claim 2,
   wherein the light guide part is provided at a position offset to one direction in the horizontal direction from a middle of the front surface of the housing in the connection posture.

6. The connector for the endoscope that is configured to be connected to the light source device generating illumination light according to claim 5,
   wherein the wireless communication device is provided in the middle of the front surface of the housing in the connection posture.

7. The connector for the endoscope that is configured to be connected to the light source device generating illumination light according to claim 2, wherein the wireless communication device is provided in the middle of the front surface of the housing in the connection posture.

8. The connector for the endoscope that is configured to be connected to the light source device generating illumination light according to claim 2, further comprising:
a grip section that is gripped by a user in a case in which the user connects the connector to the light source device,
wherein the grip section protrudes from a rear surface of the housing in the connection posture.

9. The connector for the endoscope that is configured to be connected to the light source device generating illumination light according to claim 1,
wherein the light guide part is provided at a position offset to one direction in the horizontal direction from a middle of the front surface of the housing in the connection posture.

10. The connector for the endoscope that is configured to be connected to the light source device generating illumination light according to claim 9,
wherein the wireless power receiver is provided at a position offset to a direction opposite to a direction in which the light guide part is offset with respect to the middle of the front surface of the housing.

11. The connector for the endoscope that is configured to be connected to the light source device generating illumination light according to claim 10,
wherein the wireless communication device is provided in the middle of the front surface of the housing in the connection posture.

12. The connector for the endoscope that is configured to be connected to the light source device generating illumination light according to claim 9,
wherein the wireless communication device is provided in the middle of the front surface of the housing in the connection posture.

13. The connector for the endoscope that is configured to be connected to the light source device generating illumination light according to claim 1,
wherein the wireless communication device is provided in the middle of the front surface of the housing in the connection posture.

14. The connector for the endoscope that is configured to be connected to the light source device generating illumination light according to claim 1, further comprising:
a grip section that is gripped by a user in a case in which the user connects the connector to the light source device,
wherein the grip section protrudes from a rear surface of the housing in the connection posture.

15. The connector for the endoscope that is configured to be connected to the light source device generating illumination light according to claim 14,
wherein the grip section is provided in the rear of the front surface of the housing in a connection direction in which the connector is connected to the light source device.

16. An endoscope system comprising:
a light source device that generates illumination light; and
a connector for the endoscope that is configured to be connected to the light source device, the connector comprising:
a light guide part that guides the illumination light;
a wireless communication device that wirelessly communicates with the light source device, wherein the wireless communication device includes a control signal transceiver and an image signal emitter;
a wireless power receiver that wirelessly receives power supplied from the light source device and comprises a coil that performs non-contact transmission;
a housing that is formed in a flat shape in which a horizontal length is longer than a vertical length in a connection posture where the connector is connected to the light source device,
wherein the light guide part, the wireless communication device, and the wireless power receiver are provided on a front surface of the housing, which faces the light source device, so as to be lined up in a horizontal direction, and
wherein the endoscope is configured to be connected to the light source device by the connector.

17. The endoscope system according to claim 16,
wherein the housing includes clean connecting caps which are not directly connected to a conduit opened toward an observation object and unclean connecting caps which are directly connected to the conduit opened toward the observation object,
the light source device includes a connection portion to which the connector is connected and which is provided on a front surface thereof,
the connection portion is provided at a position offset to one direction in the horizontal direction from a middle of the front surface of the light source device,
the unclean connecting caps are provided on a position of the housing offset to the direction same as the direction in which the connection portion is offset and the clean connecting caps are provided on a position of the housing offset to the direction opposite to the direction in which the connection portion is offset in the connection posture.

18. The endoscope system according to claim 17,
wherein the clean connecting caps are provided on a surface of the housing corresponding to the middle of the front surface of the light source device in the connection posture.

19. The endoscope system according to claim 17,
wherein the number of the clean connecting caps is larger than the number of the unclean connecting caps, and
the clean connecting caps are provided on a surface of the housing corresponding to the middle of the front surface of the light source device.

20. The endoscope system according to claim 17,
wherein the number of the clean connecting caps is smaller than the number of the unclean connecting caps, and
the unclean connecting caps are provided on a surface of the housing corresponding to the middle of the front surface of the light source device.

* * * * *